United States Patent [19]

Hickok et al.

[11] Patent Number: 5,704,787
[45] Date of Patent: Jan. 6, 1998

[54] HARDENED ULTRASONIC DENTAL SURGICAL TIPS AND PROCESS

[75] Inventors: Teresa R. Hickok; Claude E. Martin, both of Chula Vista, Calif.

[73] Assignee: San Diego Swiss Machining, Inc., Chula Vista, Calif.

[21] Appl. No.: 546,336

[22] Filed: Oct. 20, 1995

[51] Int. Cl.$^6$ .................................................. A61C 3/06
[52] U.S. Cl. ...................... 433/166; 433/119; 427/250; 427/299
[58] Field of Search ............................... 433/165, 166, 433/119; 427/250, 299, 307, 318, 327, 328

[56] References Cited

U.S. PATENT DOCUMENTS

| | | | |
|---|---|---|---|
| 2,562,587 | 7/1951 | Swearingen | 51/295 |
| 2,831,132 | 4/1958 | Jackson | 310/26 |
| 2,921,372 | 1/1960 | Bodine | 32/27 |
| 3,937,990 | 2/1976 | Winston | 310/8.3 |
| 4,353,696 | 10/1982 | Bridges | 433/125 |
| 4,681,541 | 7/1987 | Snaper | 433/165 |
| 4,731,019 | 3/1988 | Martin | 433/119 |
| 4,746,563 | 5/1988 | Nakano et al. | 428/216 |
| 4,803,127 | 2/1989 | Hakim | 428/457 |
| 4,981,756 | 1/1991 | Rhandhawa | 428/336 |
| 5,090,969 | 2/1992 | Oki et al. | 51/295 |
| 5,139,537 | 8/1992 | Julien | 51/293 |
| 5,145,739 | 9/1992 | Sarin | 428/336 |
| 5,244,390 | 9/1993 | Lazzara et al. | 433/143 |
| 5,266,389 | 11/1993 | Omori et al. | 428/216 |
| 5,330,481 | 7/1994 | Hood et al. | 606/99 |
| 5,366,579 | 11/1994 | Yamazaki et al. | 156/247 |
| 5,376,444 | 12/1994 | Grotepass et al. | 428/336 |
| 5,466,626 | 11/1995 | Armacost et al. | 437/60 |
| 5,507,760 | 4/1996 | Wynne et al. | 606/159 |

FOREIGN PATENT DOCUMENTS

| | | |
|---|---|---|
| 31 50039 A1 | 12/1981 | Germany . |
| 1744148 A1 | 6/1990 | Russian Federation . |
| WO 93/24676 | 5/1992 | WIPO . |

*Primary Examiner*—John J. Wilson
*Attorney, Agent, or Firm*—Baker, Maxham, Jester & Meador

[57] ABSTRACT

An ultrasonic dental tip that is hardened by a novel process that includes roughing the tip and then applying a metal nitride coating, such as titanium nitride (Ti—N) or zirconium nitride (Zr—N). The roughing is preferably accomplished by sandblasting the tip with a microblaster. Optionally the tip may be heat treated after it has been roughened and prior to being coated in order to further increase its hardness.

23 Claims, 2 Drawing Sheets

HARDENED ULTRASONIC DENTAL SURGICAL TIPS AND PROCESS

BACKGROUND OF THE INVENTION

1. Field of the Invention

This invention relates generally to ultrasonic dental surgical tips and more specifically to a surface hardening process for the tips.

2. Description of the Related Art

Dental surgeons commonly use a tip coupled to an ultrasonic generator for operations on teeth, bones, and soft tissue including dislodging and removal of dental material. With the exception of diamond coated tips, which are very expensive, the tips are smooth on the end that contacts the patient's mouth. Because the tips are smooth they have no cutting edge. Instead they rely on the ultrasonic vibrations to impart a hammering or chipping force action the target surface to dislodge material for removal.

The chipping motion has several negative qualities associated with it. One is that the steady shock can cause microfractures in teeth and bones, eventually leading to decay, soreness, and possibly loss of teeth. Another negative is that the patient experiences discomfort during the operation because of the steady knocking. Still another disadvantage is that these steady vibrations cause fatigue in the operator, reducing the time that he or she may devote to operations without rest periods.

As briefly mentioned above, one attempt by the prior art to alleviate some of the above-mentioned problems has been to use abrasive diamond coatings. The diamond surface is abrasive and therefore is able to cut bone, tissue, or teeth so no hammering action is required. In that vein, U.S. Pat. No. 5,376,444 to Grotepass et al. discloses diamond coated surgical drills and burrs with hard coatings such as titanium nitride (Ti—N). The hard coating applied over the diamond coat is intended to compress the diamond coat to prevent fracturing it. Another patent disclosing the use of a diamond coating is U.S. Pat. No. 4,731,019 to Martin. It discloses coating an ultrasonic dental instrument for scaling with diamond particles.

Unfortunately, diamond coated tips are very expensive, owing to the high cost of diamonds. Another disadvantage is that the tips usually have a fairly wide cross-sectional area because of the thickness of the diamond coating. In the case of a diamond coating plus an additional Ti—N coating the thickness is even greater. The thickness is undesirable because it limits the applications that the diamond coated tips can be used for. In particular, an important emerging dentistry field is the field of microsurgery where operations are performed under the microscope. Clearly, there is a need for hard low-cost abrasive dental surgical tips for microsurgeons but the prior art had not provided any.

The prior art has recognized the benefit of applying a hard coating, such as Ti—N, to increase the durability of medical instruments. In addition to the art referenced above, U.S. Pat. No. 5,330,481 to Hood et al. discloses an ultrasonic apparatus for implantation and extraction of a prosthetic comprising an acoustic transfuser and adapter, each coated with T—N. U.S. Pat. No. 4,681,541 to Snaper describes a dental bur having a suitable nitride deposited on the surface to enhance durability. The nitrides are disclosed as being selected from a group including Ti—N. Unfortunately, applying such a coating to the surface of a smooth dental tip exacerbates the problems caused by the vibrations because it simply increases the hardness of the hammering tip.

SUMMARY OF THE INVENTION

An objective of this invention is to provide a hardened ultrasonic dental surgical tip that is capable of cutting or abrading without the expense of prior art diamond coated tips. Another objective is to provide a tip having those advantages that can be made small enough for microsurgery. To meet these objectives, this invention provides a novel embodiment of an ultrasonic dental tip that has been roughened to create an abrasive surface and then hard surfaced with a coating of a metallic nitride according to a never before known process. The roughing process is preferably done by sandblasting the tip with a microblaster. The metallic element in the coating is preferably selected from a group consisting of Zirconium and Titanium.

An optional step in the process of this invention includes a heat-treating step applied between the roughing and coating step. The heat-treating hardens the tip further by changing its internal grain structure. Other objects and advantages of this invention will be readily appreciated upon reading the following description in view of the accompanying drawings.

BRIEF DESCRIPTION OF THE DRAWING

The objects, advantages and features of the present invention will be more clearly understood by reference to the following detailed disclosure when read in conjunction with the accompanying drawing, in which.

DETAILED DESCRIPTION OF THE PREFERRED EMBODIMENT

Figure 1:
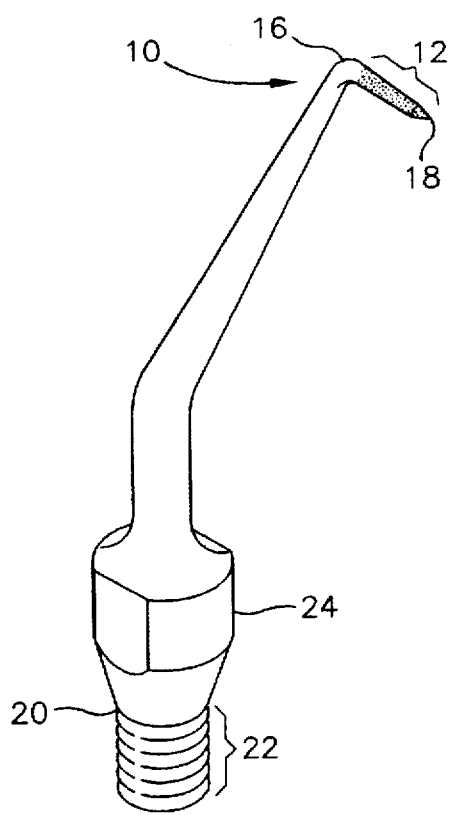
FIG. 1 is an isometric view of an ultrasonic dental tip roughened according to the process of this invention.

This invention is described with reference to a preferred embodiment shown in the drawing figures. In these figures, a like number shown in various figures represents the same or similar elements in each figure. While this invention is described in terms of the best mode for achieving this invention's objectives, it will be appreciated by those skilled in the art that variations may be accomplished in view of these teachings without deviating from the spirit or scope of the invention.

Figure 3:
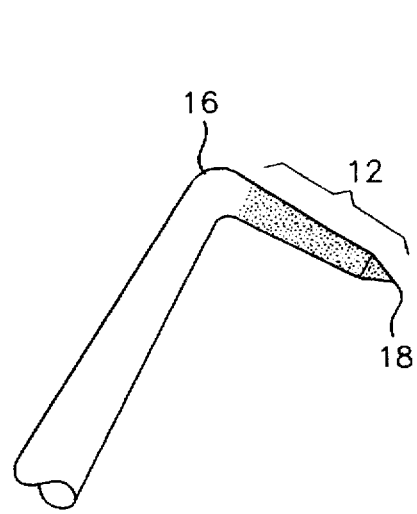
FIG. 3 is an enlarged view of the toughened portion of the tip of FIG. 1.
Figure 4:
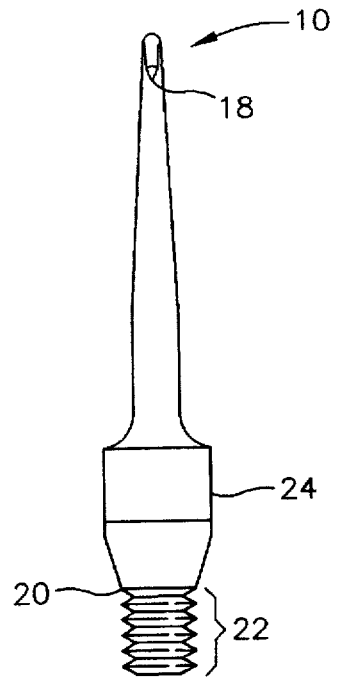
FIG. 4 is a side view of the tip of FIG. 2.

Referring to FIGS. 1 and 3 a roughened tip is shown. FIG. 1 shows an ultrasonic dental tip 10 with a roughened area 12 extending from near curved radius portion 16 to pointed end 18. FIG. 3 provides an enlarged view of the roughened area. The roughened area provides a coarse abrasive surface that will cut along any part of the roughened surface. An example of a way to create the rough area is described below; however, it will be understood by those skilled in the art that any technique for creating a roughened or coarse face on the working end of the tip will be satisfactory.

Preferably the roughing is performed by sand blasting the desired area with a microetcher or microblaster using approximately 400 grit powder. A suitable choice for such a sandblaster is provided by Danville Engineering Inc., of Danville Calif., and is available by the model name of "S-2 Precision Microsandblaster." It is preferable to operate the sandblaster by supplying pneumatic pressure of about 60–120 pounds-per-square inch, although it will be apparent to one skilled in the art that a suitable hydraulic pressure could be provided.

Figure 2:
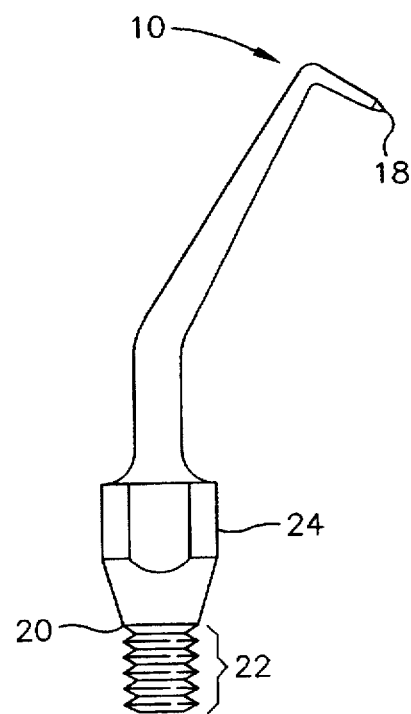
FIG. 2 is a front plan view of the tip of FIG. 1 having a metal nitride coating applied according to the process of this invention.

Reference is made to FIG. 2 below. Once the roughened area is created, then a hard coating of a metal nitride can be applied to the tip 10. It is preferable to apply the metal nitride coating from the end 20 of threads 22 to the pointed end 18 covering the entire surface area of the tip including the rough area. At a minimum the roughened area should be coated to achieve maximum hardness at the working part of the tip but it is easiest to simply coat from the threads up. The addition of the metal nitride coating to the roughened area creates an abrasive hard cutting area that is very durable and much less expensive than prior art diamond coated tips or tips having diamond abrasives imbedded therein.

The metal nitride can be applied very thinly and still imparts excellent hardness properties in contrast to the relatively thick diamond coatings of the prior art that are required to gain hardness. The thin coating is desirable because the tips do not have to support the weight of the diamond abrasive, allowing for smaller diameter tips. Additionally, the small size allows the tip to access hard to reach areas that were not reachable with prior art tips. The small size also allows for a less intrusive invasion of the subject, for example, a smaller filling may be added to a tooth.

FIG. 3 shows a side view of the tip of FIG. 2, in which it can be appreciated that the metal coating is preferably applied over the entire tip 10 with the exception of threads 22. A wrench flat area 24 is also shown, but it will be appreciated that the geometric configuration of the tip is not of particular importance to this invention, although very narrow dimensions are made possible by the process of this invention. It will be further appreciated that any coupling means other than threads may be used to enable the tip to have motion induced by the generator.

Ultrasonic generators are well known in the art and the particular type being employed with a tip of this invention is not of particular importance so the generator is not shown in the drawing figures.

Figure 5:
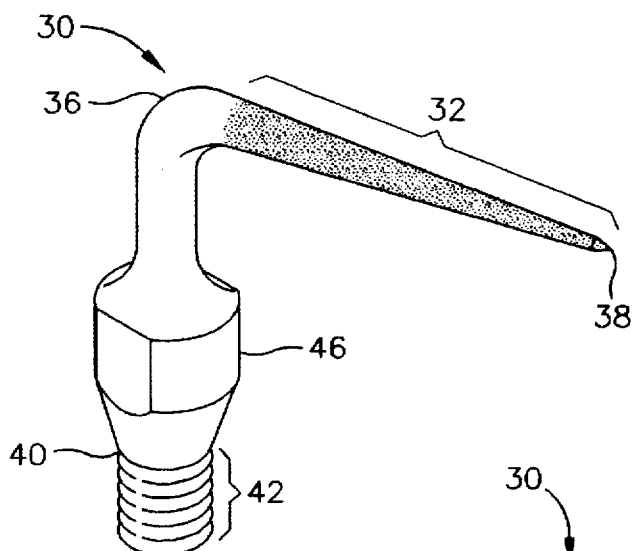
FIG. 5 is an isometric view of another embodiment of an ultrasonic dental tip roughened according to the process of this invention.
Figure 6:
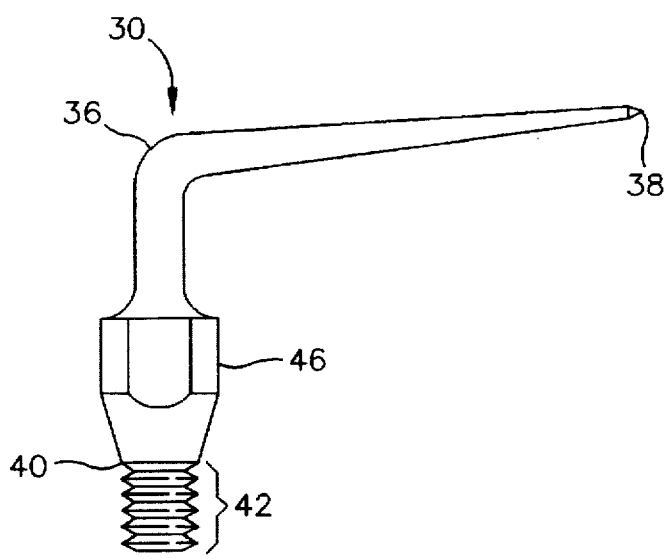
FIG. 6 is a front plan view of the tip of FIG. 5 having a metal nitride coating applied according to the process of this invention.
Figure 7:
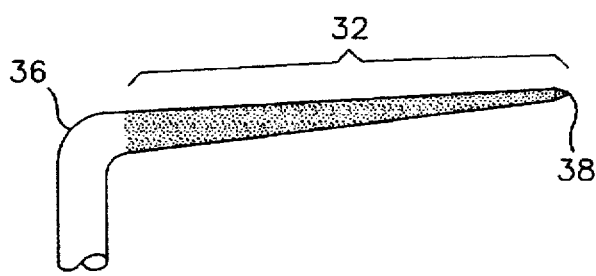
FIG. 7 is an enlarged view of the roughened portion of the tip of FIG. 5.

FIGS. 5, 6, and 7 show another embodiment of a tip 30 created by the process of this invention. FIG. 5 shows the tip 30 having a rough area 32 extending from pointed end 38 to curved portion 36. For the sake of clarity, FIG. 7 shows an enlarged view of the roughened portion of the tip. The rough area is preferably created according to the sandblasting process described above. FIG. 6 shows the same tip after a hard coating of a metal nitride is applied in the same manner as described above with reference to FIG. 2. The hard coating is preferably applied from the end 40 of threads 42 to the pointed end 38. It will be apparent to those skilled in the art that the geometric configuration of the tip is not of particular importance but the embodiment of FIGS. 5 and 6 are shown to illustrate a example of a tip which can be created according to the process of this invention.

Figure 8:
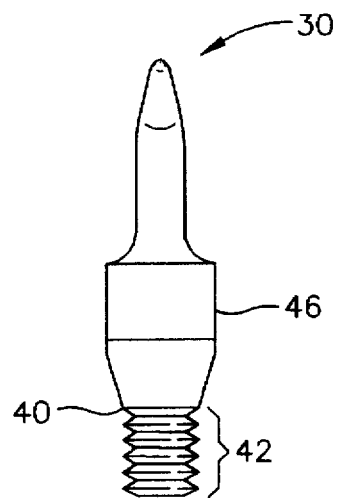
FIG. 8 is a side view of the tip of FIG. 5.

FIG. 8 shows a side view of the tip of FIG. 5 which shows a wrench flat area 46 which is considered optional. In a similar manner to that described above with reference to FIG. 3, it will be appreciated that the threads 42 are just one example of coupling means to an ultrasonic generator.

In general, the preferred overall process for creating the tips is as follows. An ultrasonic dental tip is manufactured, bent into the proper shape, and roughened by an externally applied abrasive process. Then, a metal nitride coating is applied to the roughened outer surface. Preferably, the metal element is selected from the group consisting of Zirconium (Zr) and Titanium (Ti). Between a Ti—N and Zr—N coating, the latter is the hardest at about 3000 Vickers while the former is about 2800 Vickers. Either is harder than carbide instruments which are commonly used in the prior art, but softer than an instrument prepared with expensive diamond abrasives. However, either metal nitride provides a very hard surface tip with far less cost than those using diamonds. Further, one can expect long wear from tips created by the process of this invention because Ti—N and Zr—N are both highly resistant to abrasion and corrosion. Zr—N has not been used as a hard coating for surgical tips prior to this invention. This invention is based to an extent on the inventors critical recognition of its desirable properties.

Preferably, the tip is comprised of a metal substrate, such as stainless steel, and in particular the inventors have recognized that ASTM 13–8 stainless steel is a good choice for the substrate. It has been further recognized by the inventors that it is beneficial to heat treat the steel after the roughing step to achieve a Rockwell-C hardness rating of about 40–42. Heat treating is a well known process that involves heating and cooling of a metal in the solid state for the purpose of obtaining certain desirable properties including increased hardness. However, prior to this invention the combination of roughing a metal dental tip and then heat treating it to create a hard durable abrasive tip had not been done. One of the benefits of using stainless steel is that it is easy to heat treat. Empirical evidence shows that good results can be obtained by subjecting 13—8 stainless steel to a temperature of about 900° degrees for about two hours.

When the roughing and heat treating is followed by the application of a metal nitride coating the result is an extremely hard tip having very desirable cutting abilities. The coating may be applied by any well-known technique in the art. While not desiring to be limited to any particular method of coating, the inventors have discovered that the well-known technique of using physical vapor deposition equipment employing cathodic arc techniques is a satisfactory way to deposit thin films of the metal nitrides on dental surgical tips. The coating is preferably applied very thinly so that its average thickness is about 0.0002 inches.

An advantage of such a thin coating is that very small diameter tips can be created that are extremely hard and yet abrasive. Such small diameter tips are desirable for microsurgery.

In view of the above description, it is possible that modifications and improvements will occur to those skilled in the art which are within the scope of the appended claims. Therefore, this invention is not to be limited in any way except by the appended claims.

What is claimed is:

1. A surgical tip for use with an ultrasonic device, the tip comprising:

a substantially elongate instrument having first and second opposite ends, the second end having an outer surface, wherein the first end has coupling means for coupling to an ultrasonic device; and the outer surface of the second end being a cutting surface defined by multiple indentations formed in the outer surface and having a coating of a metal nitride applied over the cutting surface to maintain its cutting character.

2. The tip of claim 1, wherein the multiple indentations are made by a sandblasting process.

3. The tip of claim 2, wherein the sandblasting process is accomplished with a microblaster employing powder having the abrasive characteristic of about 400 grit.

4. The tip of claim 1, wherein the metal nitride coat applied to the outer surface has an average thickness of about 0.0002 inches.

5. The tip of claim 1, wherein the metal member of the metal nitride is selected from the group consisting of Titanium (Ti) and Zirconium (Zr).

6. The tip of claim 1, wherein the metal nitride is Titanium nitride (Ti—N).

7. The tip of claim 6, wherein the outer surface of the tip has a surface hardness of about 2800 Vickers.

8. The tip of claim 1, wherein the metal nitride is Zirconium nitride (Zr—N).

9. The tip of claim 8, wherein the outer surface of the tip has a surface hardness of about 3000 Vickers.

10. The tip of claim 1, wherein the instrument is composed of stainless steel.

11. The tip of claim 10, wherein the instrument is heat treated to about 40–42 Rockwell-C hardness prior to applying the metal nitride coating.

12. A method for hardening surgical tips having an outside surface and adapted for use with ultrasonic devices, the method comprising the steps of:

forming a cutting surface by roughing the outside surface of the tip by forming multiple minute depressions in the surface with an externally applied abrasive process; and applying a coating of a metal nitride over the roughened cutting surface to maintain the cutting surface.

13. The method of claim 12, wherein the externally applied abrasive process used for roughing the outer surface is a sandblasting process.

14. The method of claim 13, wherein the sandblasting process is accomplished with a microblaster employing powder having the abrasive characteristic of about 400 grit.

15. The method of claim 12, wherein the metal nitride coat applied to the outer surface has an average thickness of about 0.0002 inches.

16. The method of claim 12, wherein the metal member of the metal nitride is selected from the group consisting of Titanium (Ti) and Zirconium (Zr).

17. The method of claim 12, wherein the metal nitride is Titanium nitride (Ti—N).

18. The method of claim 17, wherein the outer surface of the method has a surface hardness of about 2800 Vickers.

19. The method of claim 12, wherein the metal nitride is Zirconium nitride (Zr—N).

20. The method of claim 19, wherein the outer surface of the method has a surface hardness of about 3000 Vickers.

21. The method of claim 12, wherein the instrument is composed of stainless steel.

22. The method of claim 21, wherein the instrument is heat treated to about 40–42 Rockwell-C hardness prior to applying the metal nitride coating.

23. The method of claim 22, wherein the heat treating is performed by subjecting the method to about 900° F. temperatures for about two hours.

* * * * *